United States Patent
Grady et al.

(10) Patent No.: US 11,622,812 B2
(45) Date of Patent: *Apr. 11, 2023

(54) SYSTEMS AND METHODS FOR CORRECTION OF ARTIFICIAL DEFORMATION IN ANATOMIC MODELING

(71) Applicant: HeartFlow, Inc., Redwood City, CA (US)

(72) Inventors: Leo Grady, Darien, CT (US); Michiel Schaap, Leiden (NL); Sophie Khem, San Francisco, CA (US); Sarah Wilkes, San Mateo, CA (US); Ying Bai, Belmont, CA (US)

(73) Assignee: HeartFlow, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/534,981

(22) Filed: Nov. 24, 2021

(65) Prior Publication Data

US 2022/0079681 A1   Mar. 17, 2022

Related U.S. Application Data

(63) Continuation of application No. 16/871,216, filed on May 11, 2020, now Pat. No. 11,213,354, which is a
(Continued)

(51) Int. Cl.
*A61B 34/10*    (2016.01)
*G16H 50/50*   (2018.01)
(Continued)

(52) U.S. Cl.
CPC .............. *A61B 34/10* (2016.02); *G06F 30/20* (2020.01); *G06K 9/6215* (2013.01);
(Continued)

(58) Field of Classification Search
CPC . A61B 34/10; A61B 2034/105; A61B 6/5258; G16B 5/00; G09B 23/303;
(Continued)

(56) References Cited

U.S. PATENT DOCUMENTS 6,980,682 B1   12/2005   Avinash
7,471,820 B2   12/2008   Yeung et al.
(Continued)

OTHER PUBLICATIONS

P. Jin Kim, et al.: "Frequency of Myocardial Bridges and Dynamic Compression of Epicardial Coronary Arteries: A comparison Between Computed Tomography and Invasive Coronary Angiography", circulation 2009; 119: pp. 1408-1416, Published Mar. 2, 2009, American Heart Association.
(Continued)

*Primary Examiner* — John B Strege
(74) *Attorney, Agent, or Firm* — Bookoff McAndrews, PLLC

(57) ABSTRACT

Systems and methods are disclosed for correcting for artificial deformations in anatomical modeling. One method includes obtaining an anatomic model; obtaining information indicating a presence of an artificial deformation of the anatomic model; identifying a portion of the anatomic model associated with the artificial deformation; estimating a non-deformed local area corresponding to the portion of the anatomic model; and modifying the portion of the anatomic model associated with the artificial deformation, based on the estimated non-deformed local area.

20 Claims, 4 Drawing Sheets

Related U.S. Application Data continuation of application No. 15/961,331, filed on Apr. 24, 2018, now Pat. No. 10,682,183, which is a continuation of application No. 15/429,026, filed on Feb. 9, 2017, now Pat. No. 9,974,616, which is a continuation of application No. 14/736,853, filed on Jun. 11, 2015, now Pat. No. 9,607,386, which is a continuation of application No. 14/577,705, filed on Dec. 19, 2014, now Pat. No. 9,081,721, which is a continuation of application No. 14/311,605, filed on Jun. 23, 2014, now Pat. No. 8,958,623.

(60) Provisional application No. 61/985,946, filed on Apr. 29, 2014.

(51) Int. Cl.

| | | |
|---|---|---|
| *G16B 5/00* | (2019.01) | |
| *G06F 30/20* | (2020.01) | |
| *G06T 7/00* | (2017.01) | |
| *G06T 7/70* | (2017.01) | |
| *G06K 9/62* | (2022.01) | |
| *G06T 7/60* | (2017.01) | |
| *G09B 9/00* | (2006.01) | |
| *G09B 23/30* | (2006.01) | |
| *A61B 6/00* | (2006.01) | |
| *G06T 13/20* | (2011.01) | |

(52) U.S. Cl.
CPC .......... *G06K 9/6267* (2013.01); *G06T 7/0012* (2013.01); *G06T 7/60* (2013.01); *G06T 7/70* (2017.01); *G09B 9/00* (2013.01); *G09B 23/303* (2013.01); *G16B 5/00* (2019.02); *G16H 50/50* (2018.01); *A61B 6/5258* (2013.01); *A61B 2034/105* (2016.02); *G06T 13/20* (2013.01); *G06T 2207/10004* (2013.01); *G06T 2207/30101* (2013.01); *G06T 2207/30104* (2013.01)

(58) Field of Classification Search
CPC ...... G09B 9/00; G06K 9/6267; G06K 9/6215; G06T 7/60; G06T 7/70; G06T 7/0012; G06T 13/20; G06T 2207/30104; G06T 2207/30101; G06T 2207/10004; G16H 50/50; G06F 17/5009
See application file for complete search history.

(56) References Cited

U.S. PATENT DOCUMENTS

| | | |
|---|---|---|
| 8,249,815 B2 | 8/2012 | Taylor |
| 8,958,623 B1 | 2/2015 | Grady |
| 9,081,721 B1 | 7/2015 | Grady |
| 9,349,178 B1 | 5/2016 | Itu |
| 9,974,616 B2 * | 5/2018 | Grady ...................... G09B 9/00 |
| 10,682,183 B2 * | 6/2020 | Grady .................. G09B 23/303 |
| 11,213,354 B2 * | 1/2022 | Grady .................... G16H 50/50 |
| 2002/0071613 A1 | 6/2002 | Ford et al. |
| 2002/0136440 A1 | 9/2002 | Yim et al. |
| 2004/0114791 A1 | 6/2004 | Atkinson |
| 2008/0085042 A1 | 4/2008 | Trofimov et al. |
| 2008/0253635 A1 | 10/2008 | Spies et al. |
| 2009/0306507 A1 | 12/2009 | Hyun et al. |
| 2011/0028843 A1 | 2/2011 | Hyun et al. |
| 2011/0038516 A1 | 2/2011 | Koehler et al. |
| 2012/0072190 A1 | 3/2012 | Sharma et al. |
| 2012/0243761 A1 | 9/2012 | Senig |
| 2013/0064428 A1 | 3/2013 | Kitamura |
| 2014/0249399 A1 | 9/2014 | Sharma et al. |
| 2014/0270430 A1 | 9/2014 | Nair |
| 2014/0355858 A1 | 12/2014 | O'Dell |
| 2016/0063175 A1 | 3/2016 | Choi |

OTHER PUBLICATIONS

Chiara Ripa, et al.: Myocardial bridging: A 'forgotten' cause of acute coronary syndrome—a case report, a case report. Int. J. Angiol, Autumn 2007; vol. 16, No. 3: pp. 115-118.
S. Leschka, MD, et al.: Myocardial Bridging: Depiction Rate and Morphology at CT Coronary Angiography—Comparison with Conventional Coronary Angiography1; Radiology: vol. 246: No. 3, Mar. 2008, pp. 754-762.
Noriko Oyama-Manabe, et al.: Non-Coronary Cardiac Findings and Pitfalls in Coronary Computed Tomography Angiography; Journal of Clinical Imaging Science, vol. 1, Issue 3, Jul.-Sep. 2011, pp. 1-7. http//circ.ahajournals.org/content/119/10/1408/F2.large.jpg.
Marchenko et al. "Vascular Editor: From Angiographic Images to 3D Vascular Models" Journal of Digital Imaging, vol. 23, No. 4 Aug. 2010: pp. 386-398.
Rossignac et al. "Surgem: Interactive patient-specific anatomy-editor for hemodynamic analysis and surgery planning" Tech Report GIT-GVU-06-15, Jan. 9, 2007.

* cited by examiner

SYSTEMS AND METHODS FOR CORRECTION OF ARTIFICIAL DEFORMATION IN ANATOMIC MODELING

RELATED APPLICATION(S)

This application is a continuation of U.S. application Ser. No. 16/871,216, filed May 11, 2020, which is a continuation of U.S. application Ser. No. 15/961,331, filed Apr. 24, 2018, now U.S. Pat. No. 10,682,183, which is a continuation of U.S. application Ser. No. 15/429,026, filed Feb. 9, 2017, now U.S. Pat. No. 9,974,616, which is continuation of U.S. application Ser. No. 14/736,853, filed Jun. 11, 2015, now U.S. Pat. No. 9,607,386, which is a continuation of U.S. application Ser. No. 14/577,705, filed Dec. 19, 2014, now U.S. Pat. No. 9,081,721, which is a continuation of U.S. application Ser. No. 14/311,605, filed Jun. 23, 2014, now U.S. Pat. No. 8,958,623, and claims priority to U.S. Provisional Application No. 61/985,946 filed Apr. 29, 2014, the entire disclosures of which are hereby incorporated by reference in their entireties.

FIELD OF THE INVENTION

Various embodiments of the present disclosure relate generally to medical modeling and related methods. More specifically, particular embodiments of the present disclosure relate to systems and methods for correcting artificial deformation in anatomic modeling.

BACKGROUND

Coronary artery disease may cause the blood vessels providing blood to the heart to develop lesions, such as a stenosis (abnormal narrowing of a blood vessel). As a result, blood flow to the heart may be restricted. A patient suffering from coronary artery disease may experience chest pain, referred to as chronic stable angina during physical exertion or unstable angina when the patient is at rest. A more severe manifestation of disease may lead to myocardial infarction, or heart attack.

A desire exists to provide more accurate data relating to coronary lesions, e.g., size, shape, location, functional significance (e.g., whether the lesion impacts blood flow), etc. Patients suffering from chest pain and/or exhibiting symptoms of coronary artery disease may be subjected to one or more tests that may provide some indirect evidence relating to coronary lesions. For example, noninvasive tests may include electrocardiograms, biomarker evaluation from blood tests, treadmill tests, echocardiography, single positron emission computed tomography (SPECT), and positron emission tomography (PET). These noninvasive tests, however, typically do not provide a direct assessment of coronary lesions or assess blood flow rates. The noninvasive tests may provide indirect evidence of coronary lesions by looking for changes in electrical activity of the heart (e.g., using electrocardiography (ECG)), motion of the myocardium (e.g., using stress echocardiography), perfusion of the myocardium (e.g., using PET or SPECT), or metabolic changes (e.g., using biomarkers).

For example, anatomic data may be obtained noninvasively using coronary computed tomographic angiography (CCTA). CCTA may be used for imaging of patients with chest pain and involves using computed tomography (CT) technology to image the heart and the coronary arteries following an intravenous infusion of a contrast agent. However, CCTA also cannot provide direct information on the functional significance of coronary lesions, e.g., whether the lesions affect blood flow. In addition, since CCTA is purely a diagnostic test, it can neither be used to predict changes in coronary blood flow, pressure, or myocardial perfusion under other physiologic states (e.g., exercise), nor can it be used to predict outcomes of interventions.

Thus, patients may require an invasive test, such as diagnostic cardiac catheterization, to visualize coronary lesions. Diagnostic cardiac catheterization may include performing conventional coronary angiography (CCA) to gather anatomic data on coronary lesions by providing a doctor with an image of the size and shape of the arteries. CCA, however, does not provide data for assessing the functional significance of coronary lesions. For example, a doctor may not be able to diagnose whether a coronary lesion is harmful without determining whether the lesion is functionally significant. Thus, CCA has led to a procedure referred to as an "oculostenotic reflex", in which interventional cardiologists insert a stent for every lesion found with CCA regardless of whether the lesion is functionally significant. As a result, CCA may lead to unnecessary operations on the patient, which may pose added risks to patients and may result in unnecessary heath care costs for patients.

During diagnostic cardiac catheterization, the functional significance of a coronary lesion may be assessed invasively by measuring the fractional flow reserve (FFR) of an observed lesion. FFR is defined as the ratio of the mean blood pressure downstream of a lesion divided by the mean blood pressure upstream from the lesion, e.g., the aortic pressure, under conditions of increased coronary blood flow, e.g., when induced by intravenous administration of adenosine. Blood pressures may be measured by inserting a pressure wire into the patient. Thus, the decision to treat a lesion based on the determined FFR may be made after the initial cost and risk of diagnostic cardiac catheterization has already been incurred.

To reduce the above disadvantages of invasive FFR measurements, methods have been developed for assessing coronary anatomy, myocardial perfusion, and coronary artery flow noninvasively. Specifically, computational fluid dynamics (CFD) simulations have been successfully used to predict spatial and temporal variations of flow rate and pressure of blood in arteries, including FFR. Such methods and systems benefit cardiologists who diagnose and plan treatments for patients with suspected coronary artery disease, and predict coronary artery flow and myocardial perfusion under conditions that cannot be directly measured, e.g., exercise, and to predict outcomes of medical, interventional, and surgical treatments on coronary artery blood flow and myocardial perfusion.

Such CFD simulations may be improved by accurately modeling blood vessels, since inaccuracies in blood vessel modeling may translate into unreliable assessments. For example, artifacts from imaging or surrounding anatomy (e.g., myocardial bridging) may influence model anatomy because artifacts may appear as deformations where there may be no pathological deformations in an actual vessel. Many types of medical assessments (e.g., measuring minimal lumen diameter, performing blood flow simulations, or calculating geometric characteristics of a blood vessel) may be compromised by inaccuracies in patient-specific anatomical (geometrical) blood vessel models. Therefore, a desire exists to construct patient-specific blood vessel models that may correct and/or account for artificial deformations from imaging when extracting a model from images. Such a form of modeling may improve the accuracy of medical assessments.

The foregoing general description and the following detailed description are exemplary and explanatory only and are not restrictive of the disclosure.

SUMMARY

According to certain aspects of the present disclosure, systems and methods are disclosed for correcting for artificial deformations in anatomical modeling. One method includes: obtaining an anatomic model; obtaining information indicating a presence of an artificial deformation of the anatomic model; identifying a portion of the anatomic model associated with the artificial deformation; estimating a non-deformed local area corresponding to the portion of the anatomic model; and modifying the portion of the anatomic model associated with the artificial deformation, based on the estimated non-deformed local area.

In accordance with another embodiment, a system for anatomical modeling comprises: a data storage device storing instructions for correcting anatomical modeling; and a processor configured for: obtaining an anatomic model; obtaining information indicating a presence of an artificial deformation of the anatomic model; identifying a portion of the anatomic model associated with the artificial deformation; estimating a non-deformed local area corresponding to the portion of the anatomic model; and modifying the portion of the anatomic model associated with the artificial deformation, based on the estimated non-deformed local area.

In accordance with yet another embodiment, a non-transitory computer readable medium for use on a computer system containing computer-executable programming instructions for correcting anatomical modeling is provided. The method includes: obtaining an anatomic model; obtaining information indicating a presence of an artificial deformation of the anatomic model; identifying a portion of the anatomic model associated with the artificial deformation; estimating a non-deformed local area corresponding to the portion of the anatomic model; and modifying the portion of the anatomic model associated with the artificial deformation, based on the estimated non-deformed local area.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

An accurate patient-specific anatomical (geometrical) blood vessel model is useful for many types of medical assessments. For example, measuring minimal lumen diameter, performing blood flow simulations, or calculating geometric characteristics of a blood vessel may be influenced by the accuracy of a blood vessel model. However, various artifacts of the imaging (if the model is extracted from an image) or surrounding anatomy may cause the vessel to have the appearance of a significant deformation when there may be no actual pathology shown by the vessel. Deformations may be due to image artifacts (e.g., misregistration, streaking artifacts, stents, pacemaker leads, surgical clips, windmill artifacts), loss of contrast (e.g., due to contrast timing error), or artificial constriction associated with tissue (e.g., myocardial bridging). In this disclosure, undesired (non-significant) deformations, due to, for example, imaging artifacts or surrounding anatomy, may be referred to as, "artificial deformations." Thus, a desire exists for correcting artificial deformations in anatomical modeling such that an accurate medical assessment may be made. The disclosure may apply to images obtained from any medical imaging modality, including CT, MR, ultrasound, IVUS, OCT, etc. Therefore, the present disclosure is further directed to a new approach for accounting for artificial deformations in modeling any anatomic, such as, for example, blood vessels.

Figure 1:
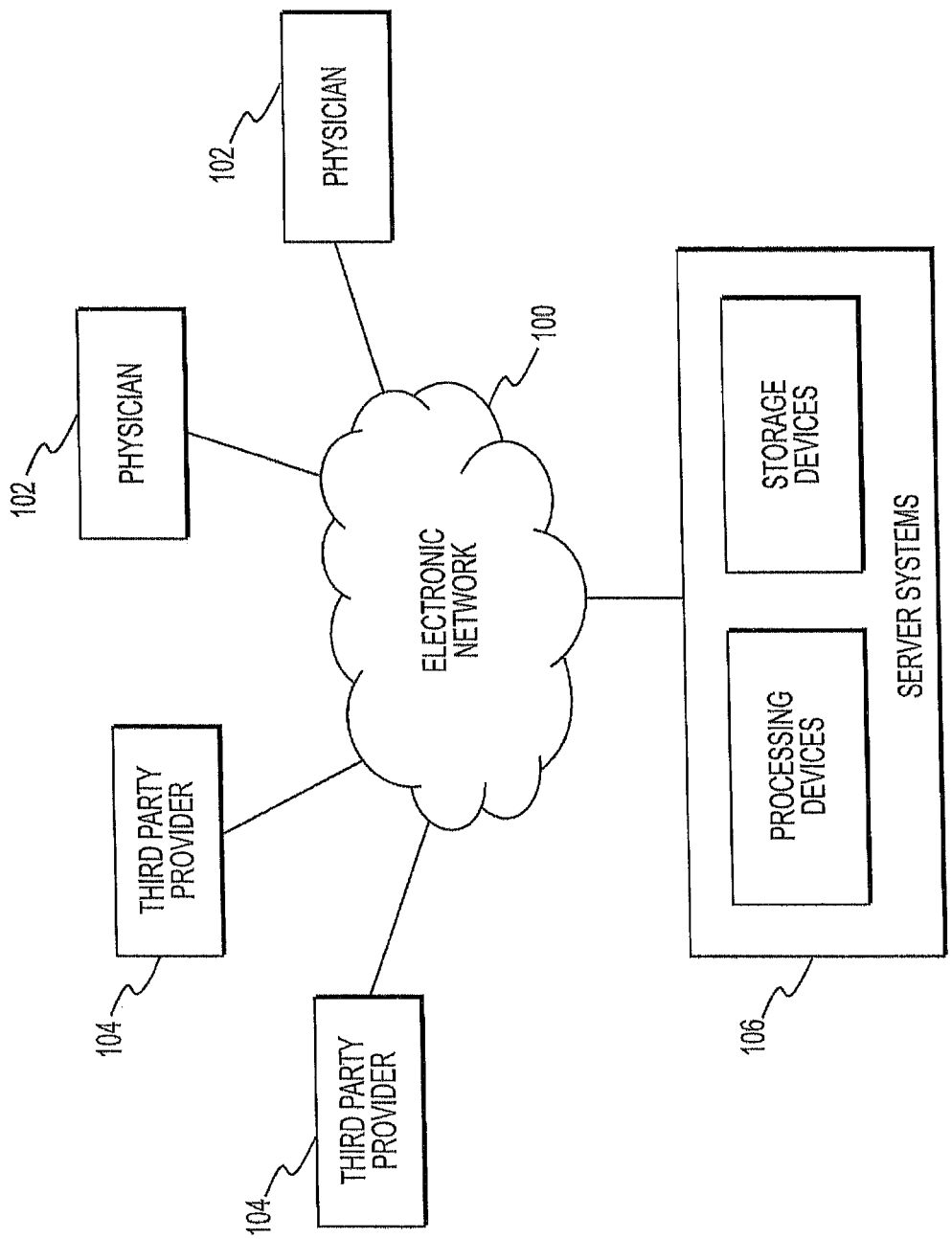
FIG. 1 is a block diagram of an exemplary system and network for correcting anatomic modeling, according to an exemplary embodiment of the present disclosure.

Referring now to the figures, FIG. 1 depicts a block diagram of an exemplary system and network for correcting artificial deformation in blood vessel modeling. Specifically, FIG. 1 depicts a plurality of physicians 102 and third party providers 104, any of whom may be connected to an electronic network 100, such as the Internet, through one or more computers, servers, and/or handheld mobile devices. Physicians 102 and/or third party providers 104 may create or otherwise obtain images of one or more patients' cardiac and/or vascular systems. The physicians 102 and/or third party providers 104 may also obtain any combination of patient-specific information, such as age, medical history, blood pressure, blood viscosity, etc. Physicians 102 and/or third party providers 104 may transmit the cardiac/vascular images and/or patient-specific information to server systems 106 over the electronic network 100. Server systems 106 may include storage devices for storing images and data received from physicians 102 and/or third party providers 104. Server systems 106 may also include processing devices for processing images and data stored in the storage devices.

Figure 2:
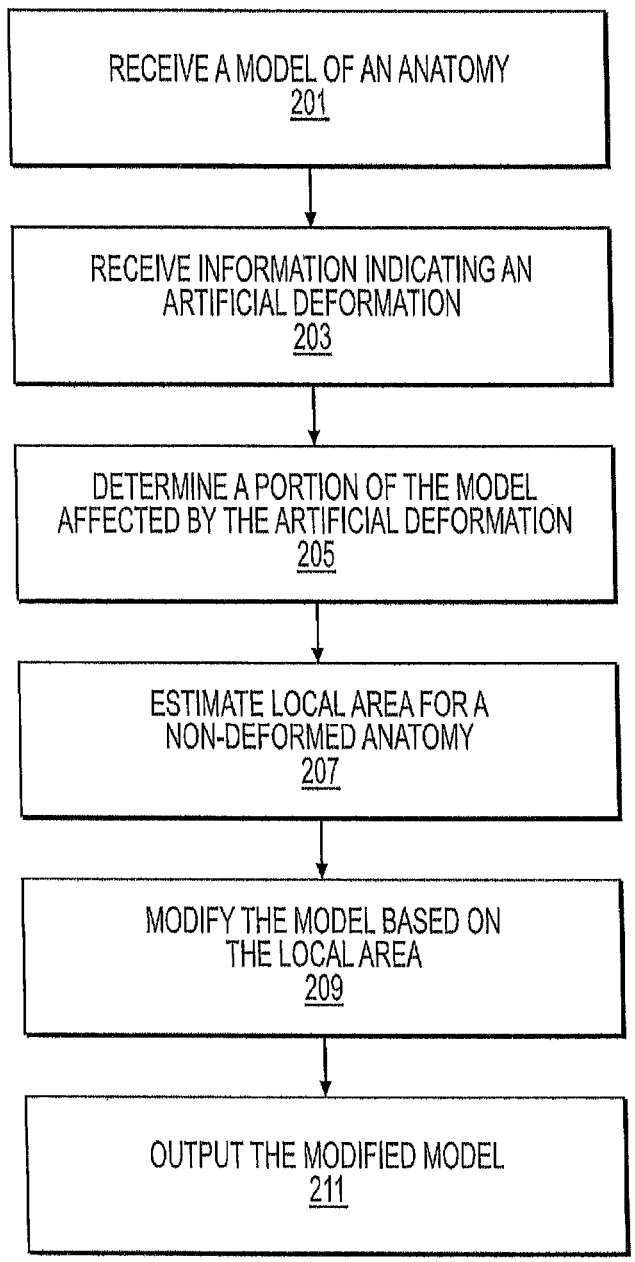
FIG. 2 is a block diagram of an exemplary method of correcting for artificial deformations in anatomic modeling, according to an exemplary embodiment of the present disclosure.

FIG. 2 is a block diagram of an exemplary method 200 of correcting for artificial deformation in anatomic modeling (e.g., blood vessel modeling), according to an exemplary embodiment. In one embodiment, step 201 may include receiving a model of anatomy that contains explicit or implicit local area information. For example, such information may include a three-dimensional model with centerline and/or area information. In one embodiment, the model may be received on an electronic storage device (e.g., hard drive, network drive, random access memory (RAM), etc.). In one embodiment, step 203 may include receiving information indicating that a portion of the vessel model has an artificial deformation. For example, such information may include computations, user input (e.g., from an operator), algorithm output(s), etc. In some instances, such information may be received, also, on an electronic storage device. In one embodiment, step 205 may include determining a portion of the anatomic model affected by the artificial deformation. Step 207 may include estimating a local area for a non-deformed anatomy in the region of the area affected by the artificial deformation. In one embodiment, step 209 may include modifying the anatomic model within the portion affected by the artificial deformation, such that the anatomic model geometry is changed to the estimated local area for a non-deformed anatomy. In some embodiments, steps 205-209 may be performed using a computational device (e.g., a computer, a laptop, a cloud computing service, a tablet, a cell phone, etc., such as, of server systems 106). Step 211 may include outputting the modified anatomic model to an electronic storage device.

Further embodiments may include performing simulations using the modified blood vessel model. For example, simulations may take into account specific patient data, imaging data, collective patient population data, etc. Medical assessments or diagnoses may be formed from simulations based on the modified blood vessel model output from method 200.

Figure 3:
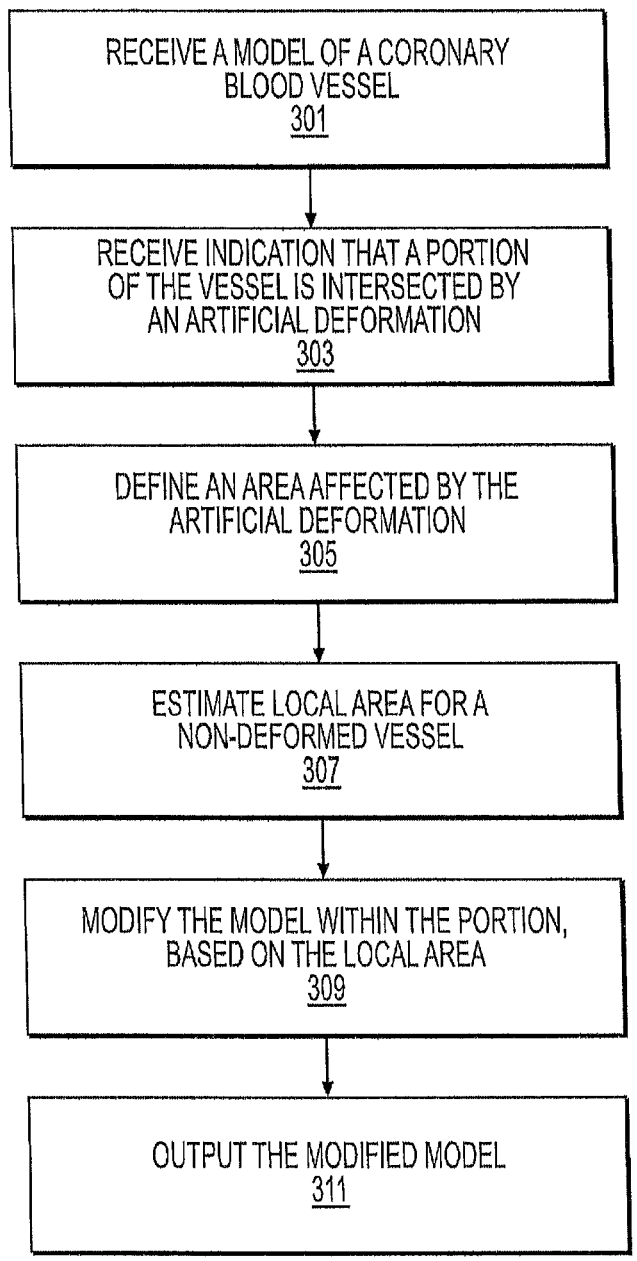
FIG. 3 is a block diagram of an exemplary method of specific embodiments for correcting various forms of artificial deformations, according to an exemplary embodiment of the present disclosure.

FIG. 3 is a block diagram of an exemplary method 300 of specific embodiments for correcting artificial deformations from various artifacts, according to an exemplary embodiment. In one embodiment, step 301 may include receiving a model of a coronary blood vessel that contains explicit or implicit local area information. For instance, step 301 may include receiving a 3-D model with centerline and/or area information. In some cases, exemplary models include 3-D geometrical models (e.g., a triangulated surface mesh or tetrahedralized 3-D mesh) or a centerline with a radius (or area) associated with each centerline point. The model may be received on an electronic storage device (e.g., a hard drive, network derive, RAM, etc. of server systems 106).

Step 303 may include receiving information indicating that a portion of the vessel model includes an artificial deformation. As previously discussed, artificial deformations may be due to image artifacts (e.g., misregistration, streaking artifacts, stents, pacemaker leads, surgical clips, windmill artifacts, etc.), loss of contrast (e.g., due to contrast timing error), and/or artificial constriction associated with tissue (e.g., myocardial bridging). The information may thus include an indication that a portion of the imaged vessel may be intersected by a misregistration, a motion artifact, and/or a portion of the myocardium.

In one embodiment, a misregistration may include artifacts caused by a slight offset between, for example, fat and water, such that different voxels may appear to indicate the fat and water, respectively, even when the fat and water may be represented as the same voxel. Misregistration may be detected by any desired means, including a normalized cross-correlation computation between neighboring slices of a computed tomography (CT) image. A misregistrartion may also be determined visually by an operator. In one embodiment, a motion artifact may cause an artificial deformation, for instance, bulging in a vessel due to blurring or ghosting from varying phase and amplitude associated with imaging acquisition. A motion artifact may be detected by several desired means, including computing a measure of local image blur in a CT and/or magnetic resonance (MR) image. Like misregistrations, motion artifacts may be determined visually by an operator. In one embodiment, a model intersected by a portion of the myocardium may cause an apparent deformation, such as, for example, a narrowing of a blood vessel. The myocardium may be detected visually by an operator or automatically, by employing an image segmentation algorithm. In one embodiment, step 303 may including receiving the information on the misregistration, motion artifact, and/or myocardium via an electronic storage device.

In one embodiment, step 305 may include defining an area affected by the artificial deformation. For example, step 305 may include defining an area affected by an artificial deformation for a portion of the vessel model near the intersection with the misregistration artifact. In some cases, the area may be determined by the magnitude of the cross-correlation value, or it may be determined visually by an operator. Alternately or in addition, step 305 may include defining an area affected by an artificial deformation for a portion of the vessel model near the intersection with the motion artifact. In some scenarios, the area may be determined by the magnitude of the measured image blur. Like a misregistration, a motion artifact may be determined visually by an operator. In yet another alternative or additional embodiment, step 305 may include defining an area affected by an artificial deformation for a portion of the vessel model near the intersection with the myocardium. For example, the area may be determined by finding the region of intersection between the vessel and the myocardium. Another means of determining the affected area may include finding a portion of vessel size that narrows near the myocardium and then returns to an expected vessel size distal to the myocardium. One embodiment for finding a region of intersection between the vessel and the myocardium may be found at FIG. 4.

In one embodiment, step 307 may include estimating a local area for a non-deformed vessel. For example, estimating the local area for a non-deformed vessel may include determining the size of the vessel outside (e.g., either proximal and/or distal to) the affected area. For example, the radius for estimating the area may be determined by measuring the radius proximal and/or distal to the deformation and computing an average radius as the estimate. The radius may also, or alternately, be estimated by using a robust kernel regression of the vessel radii along the centerline to determine an idealized radius in the affected region. In such a case employing robust kernel regression, the idealized radius may be determined with respect to a conditional probability distribution, given the centerline. The radius may also be estimated by referring to a database of similar patients, vessels, and locations when no deformation occurred. In the presence of a bifurcation within the affected area, the estimated radii for both branches of the bifurcation may be set to fit Murray's Law.

In one embodiment, step 309 may include modifying the blood vessel model within the portion affected by the artificial deformation, where the modification may include changing the affected portion of the blood vessel model to match the estimated local area for a non-deformed vessel. The modification may be performed using several methods. For example, one method may include creating a model with a constant radius centered on the centerline. The radius may be the radius determined from step 307. Another method may include smoothly interpolating the model radius between the proximal and distal regions of the affected region. Yet another method may include matching the radius with an idealized radius. In some cases, the idealized radius may be obtained via kernel estimation or via the reference database of similar patients. In one embodiment, steps 305-309 may be performed using a computational device (e.g., a computer, a laptop, a cloud computing service, a tablet, a cell phone, etc., such as server systems 106). Step 311 may include outputting the modified blood vessel model to an electronic storage device.

Figure 4:
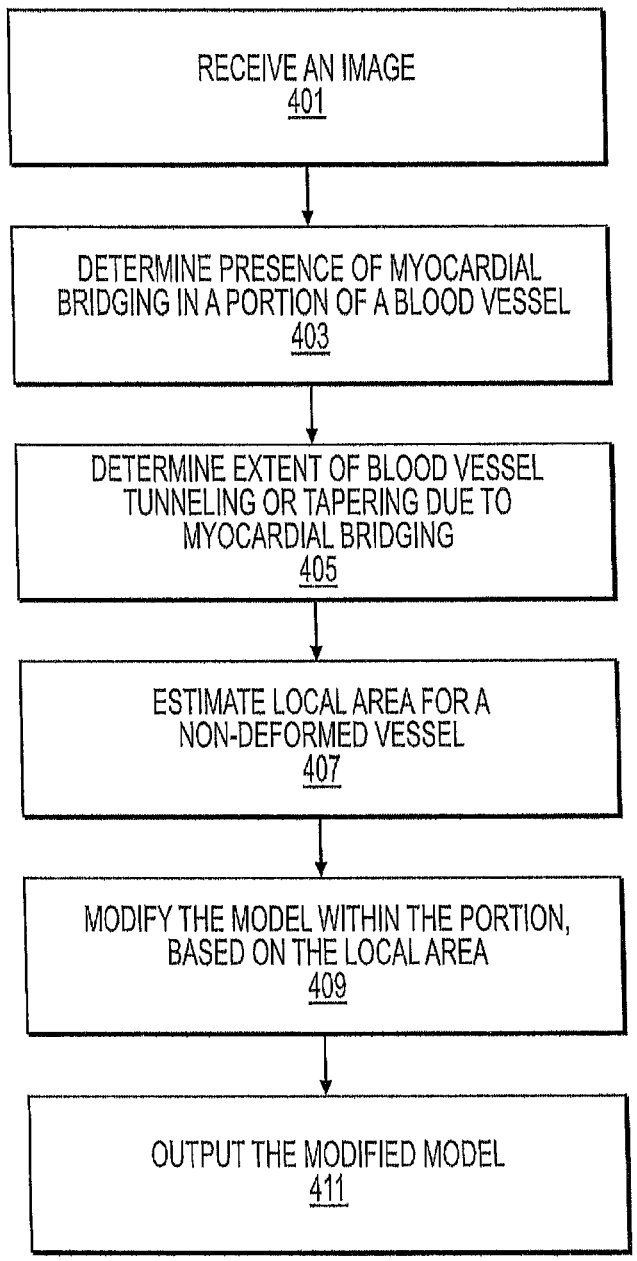
FIG. 4 is a block diagram of an exemplary method of receiving information regarding myocardial bridging, according to an exemplary embodiment of the present disclosure.

FIG. 4 is a block diagram of an exemplary method 400 of receiving information regarding myocardial bridging, according to an exemplary embodiment. Specifically, method 400 may include finding a region of intersection between a vessel and a myocardium. In one embodiment, step 401 may include an image, e.g., a three-dimensional CT volume. Next, step 403 may include finding myocardial bridging based on the image. For instance, step 403 may include distinguishing between fat and the myocardium. While fat may not constrict a vessel, the myocardium or other fibrous tissue may, so differentiating between the myocardium and fat may dictate whether to modify an anatomic model. In one embodiment, step 403 may include analyzing Hounsfield scale (HU) measurements in regions of images surrounding vessels. Fat may have a lower HU than the myocardium. Thus, comparisons of images based on local radiodensity may indicate that a vessel is surrounded by fat rather than the myocardium (or vice versa). Myocardial bridging may exist when myocardium is touching an artery. Therefore, step 403 may further include determining whether a myocardium is in contact with vessel.

If contact between a myocardium and a vessel is detected, step 405 may include determining the extent of the contact. For instance, myocardial bridging may include when myocardial tissue completely surrounds a vessel and/or where a circumference of a vessel is partly surrounded by myocardial tissue, to the extent that the myocardium causes a tapering and/or reduction of cross-sectional area of at least a portion of the vessel. Step 405 may include finding an extent of myocardial bridging by way of tunneling (e.g., amount that vessel dips into muscle of the myocardium) and/or tapering in vessels. Step 407 may further include computing a radius and/or local area for a non-bridged region or portion of the vessel. Step 409 may include modifying the blood vessel model within the bridged portion, based on radius and/or local area computed in step 407. For example, modifications may include changing the affected portion of the blood vessel model to reflect the estimated local area for a non-deformed vessel. Methods described in step 309 may also be used for making the modifications in step 409. For example, modifying the blood vessel model in step 409 may also include creating a model with a constant radius centered on the centerline (e.g., using a radius computed in step 407), interpolating model radius between proximal and distal portions of an affected region of a model, matching a radius to an idealized radius, obtaining a radius via a kernel estimation or via the reference database of similar patients, etc. In one embodiment, steps 405-409 may be performed using a computational device (e.g., a computer, a laptop, a cloud computing service, a tablet, a cell phone, etc., such as server systems 106). Step 411 may include outputting the modified blood vessel model to an electronic storage device. In some embodiments, method 400 may be performed based on user input. In other embodiments, portions of method 400 may be automated and/or computer-assisted.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A computer-implemented method of correcting anatomical modeling, the method comprising:
   obtaining a plurality of patient-specific images including a vessel and a portion of myocardial tissue;
   obtaining a vessel model including the vessel and the portion of myocardial tissue;
   determining a bridged portion within the portion of myocardial tissue based on the plurality of patient-specific images;
   comparing a local radiodensity within the plurality of patient-specific images of the vessel;
   computing a radius or local area for a non-bridged portion of the vessel; and
   modifying the vessel model within the bridged portion of myocardial tissue based on the computed radius or local area.

2. The method of claim 1, further including:
   performing one or more simulations using the modified vessel model.

3. The method of claim 2, further including
   providing a medical assessment based on the one or more simulations.

4. The method of claim 1, wherein the vessel model includes implicit or explicit local area information.

5. The method of claim 1, wherein modifying the vessel model includes creating an updated vessel model with the computed radius centered on a centerline.

6. The method of claim 1, further including:
   outputting the modified vessel model to an electronic storage device.

7. The method of claim 1, wherein comparing the local radiodensity determines whether the portion of the myocardial tissue is in contact with the vessel.

8. The method of claim 1, wherein determining the bridged portion includes determining the bridged portion via tunneling.

9. A system for correcting anatomical modeling, the system comprising:
   a data storage device storing instructions for correcting anatomical modeling; and
   a processor configured to execute the instructions to perform operations comprising:
      obtaining a plurality of patient-specific images including a vessel and a portion of myocardial tissue;
      obtaining a vessel model including the vessel and the portion of myocardial tissue;
      determining a bridged portion within the portion of myocardial tissue based on the plurality of patient-specific images;
      comparing a local radiodensity within the plurality of patient-specific images of the vessel;
      computing a radius or local area for a non-bridged portion of the vessel; and
      modifying the vessel model within the bridged portion of myocardial tissue based on the computed radius or local area.

10. The system of claim 9, the operations further comprising:
   performing one or more simulations using the modified vessel model.

11. The system of claim 10, the operations further comprising:
  providing a medical assessment based on the one or more simulations.

12. The system of claim 9, wherein the vessel model includes implicit or explicit local area information.

13. The system of claim 9, wherein modifying the vessel model includes creating an updated vessel model with the computed radius centered on a centerline.

14. The system of claim 9, the operations further comprising:
  outputting the modified vessel model to an electronic storage device.

15. The system of claim 9, wherein comparing the local radiodensity determines whether the portion of the myocardial tissue is in contact with the vessel.

16. The system of claim 9, wherein determining the bridged portion includes determining the bridged portion via tunneling.

17. A non-transitory computer readable medium for use on a computer system containing computer-executable programming instructions for performing operations correcting anatomical modeling, the operations comprising:
  obtaining a plurality of patient-specific images including a vessel and a portion of myocardial tissue;
  obtaining a vessel model including the vessel and the portion of myocardial tissue;
  determining a bridged portion within the portion of myocardial tissue based on the plurality of patient-specific images;
  comparing a local radio density within the plurality of patient-specific images of the vessel;
  computing a radius or local area for a non-bridged portion of the vessel; and
  modifying the vessel model within the bridged portion of myocardial tissue based on the computed radius or local area.

18. The non-transitory computer readable medium of claim 17, wherein the operations further comprise:
  performing one or more simulations using the modified vessel model.

19. The non-transitory computer readable medium of claim 18, wherein the operations further comprise:
  providing a medical assessment based on the one or more simulations.

20. The non-transitory computer readable medium of claim 17, wherein the vessel model includes implicit or explicit local area information.

* * * * *